United States Patent
Amir

(10) Patent No.: US 9,760,020 B2
(45) Date of Patent: Sep. 12, 2017

(54) IN-SITU METROLOGY

(71) Applicant: KLA-Tencor Corporation, Milpitas, CA (US)

(72) Inventor: Nuriel Amir, St. Yokneam (IL)

(73) Assignee: KLA-Tencor Corporation, Milpitas, CA (US)

(*) Notice: Subject to any disclaimer, the term of this patent is extended or adjusted under 35 U.S.C. 154(b) by 399 days.

(21) Appl. No.: 14/162,110

(22) Filed: Jan. 23, 2014

(65) Prior Publication Data

US 2014/0139815 A1    May 22, 2014

Related U.S. Application Data

(63) Continuation of application No. PCT/US2013/071143, filed on Nov. 21, 2013.

(60) Provisional application No. 61/729,327, filed on Nov. 21, 2012.

(51) Int. Cl.
*G03F 7/20* (2006.01)
*G01N 21/47* (2006.01)
*G01N 21/95* (2006.01)

(52) U.S. Cl.
CPC ..... *G03F 7/70633* (2013.01); *G01N 21/4788* (2013.01); *G01N 21/9501* (2013.01); *G03F 7/70141* (2013.01); *G03F 7/70616* (2013.01)

(58) Field of Classification Search
CPC ............ G01N 21/4788; G01N 21/9501; G03F 7/70141; G03F 7/70616; G03F 7/70633; G03F 7/70625
See application file for complete search history.

(56) References Cited

U.S. PATENT DOCUMENTS

| | | | | |
|---|---|---|---|---|
| 5,783,342 A | * | 7/1998 | Yamashita | ............... G03F 9/70 356/511 |
| 6,150,231 A | * | 11/2000 | Muller | ............... G03F 7/70633 438/401 |
| 6,301,009 B1 | | 10/2001 | Tinker | |
| 6,356,345 B1 | | 3/2002 | McArthur et al. | |
| 7,076,321 B2 | | 7/2006 | Purdy | |

(Continued)

FOREIGN PATENT DOCUMENTS

| | | | |
|---|---|---|---|
| EP | 1063570 A3 | 12/2000 | |
| EP | 1402569 A2 | 3/2004 | |

(Continued)

OTHER PUBLICATIONS

Spanos, C.J. "The economic impact of choosing off-line, inline or in situ metrology deployment in semiconductor manufacturing," Dept. of Electr. Eng., California Univ., Berkeley, CA USA, 2001 IEEE Semiconductor Manufacturing Symposium, 2001 IEEE International; Conference; http://ieeexplore.ieee.org/xpl/articleDetails.jsp?tp=&arnumber=962909&contentType=Conference+Publications&searchField%3DSearch_All%26queryText%3DIn-situ+Metrology.

*Primary Examiner* — Steven H Whitesell Gordon
(74) *Attorney, Agent, or Firm* — Suiter Swantz pc llo

(57) ABSTRACT

Metrology methods and systems are provided, which measure metrology targets during the exposure stage using reflected or diffracted exposure illumination or additional simultaneous illumination having longer wavelengths than the exposure illumination. The metrology measurements are used to correct the lithographic process in a short loop, enabling realtime and even predictive error correction. The metrology methods, tools and systems also include defect detection during the exposure stage.

44 Claims, 8 Drawing Sheets

(56) References Cited

U.S. PATENT DOCUMENTS

| | | | |
|---|---|---|---|
| 7,302,367 B2 | 11/2007 | Li et al. | |
| 7,482,178 B2 | 1/2009 | Mui et al. | |
| 7,499,183 B2 | 3/2009 | Maznev | |
| 8,274,645 B2 | 9/2012 | Davis et al. | |
| 2004/0101983 A1* | 5/2004 | Jones | H01L 22/20 |
| | | | 438/14 |
| 2004/0147048 A1 | 7/2004 | Jakatdar et al. | |
| 2004/0233443 A1 | 11/2004 | Mieher et al. | |
| 2005/0181571 A1* | 8/2005 | Lin | G03F 7/70633 |
| | | | 438/377 |
| 2005/0193362 A1* | 9/2005 | Phan | G01N 21/95607 |
| | | | 430/22 |
| 2009/0170024 A1* | 7/2009 | Hennig | G03F 7/70633 |
| | | | 430/270.1 |

FOREIGN PATENT DOCUMENTS

| | | |
|---|---|---|
| EP | 1451867 A2 | 9/2004 |
| EP | 1659452 A1 | 5/2006 |
| EP | 1739493 A1 | 1/2007 |
| EP | 1862856 A1 | 12/2007 |
| EP | 1636835 B1 | 10/2011 |
| JP | 2011528864 | 11/2011 |
| WO | 02082534 A2 | 10/2002 |

\* cited by examiner

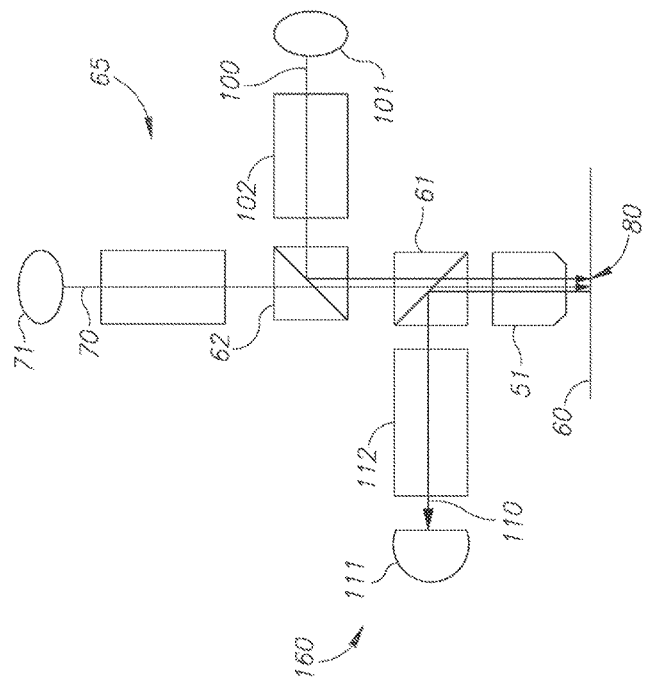
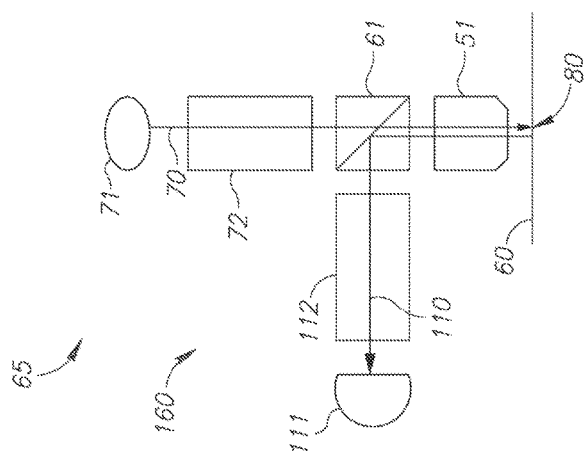
Figure 2B
Figure 2A

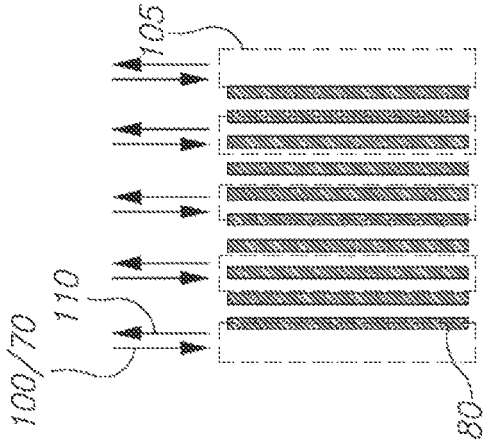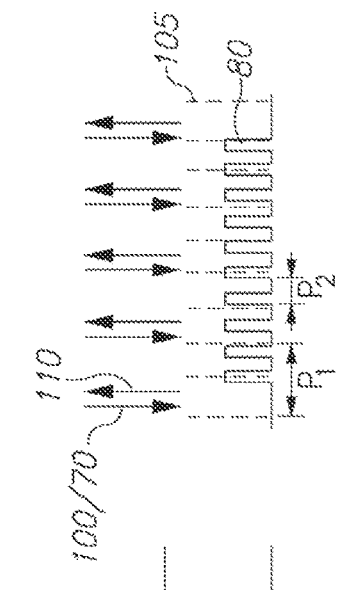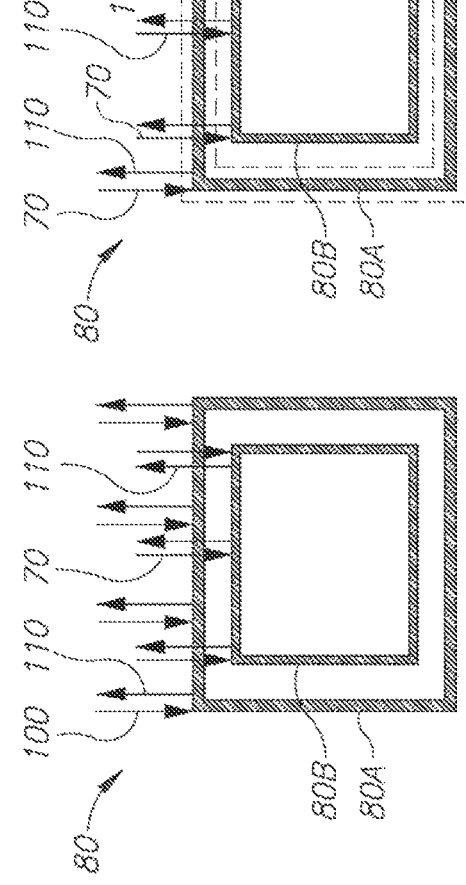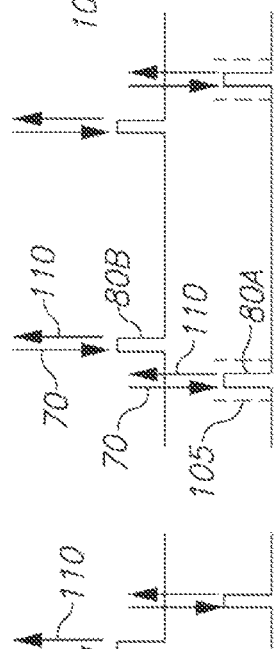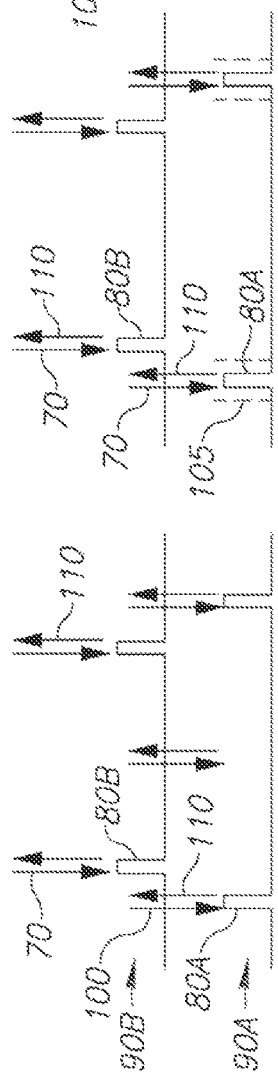
Figure 3A   Figure 4A   Figure 5A
Figure 3B   Figure 4B   Figure 5B

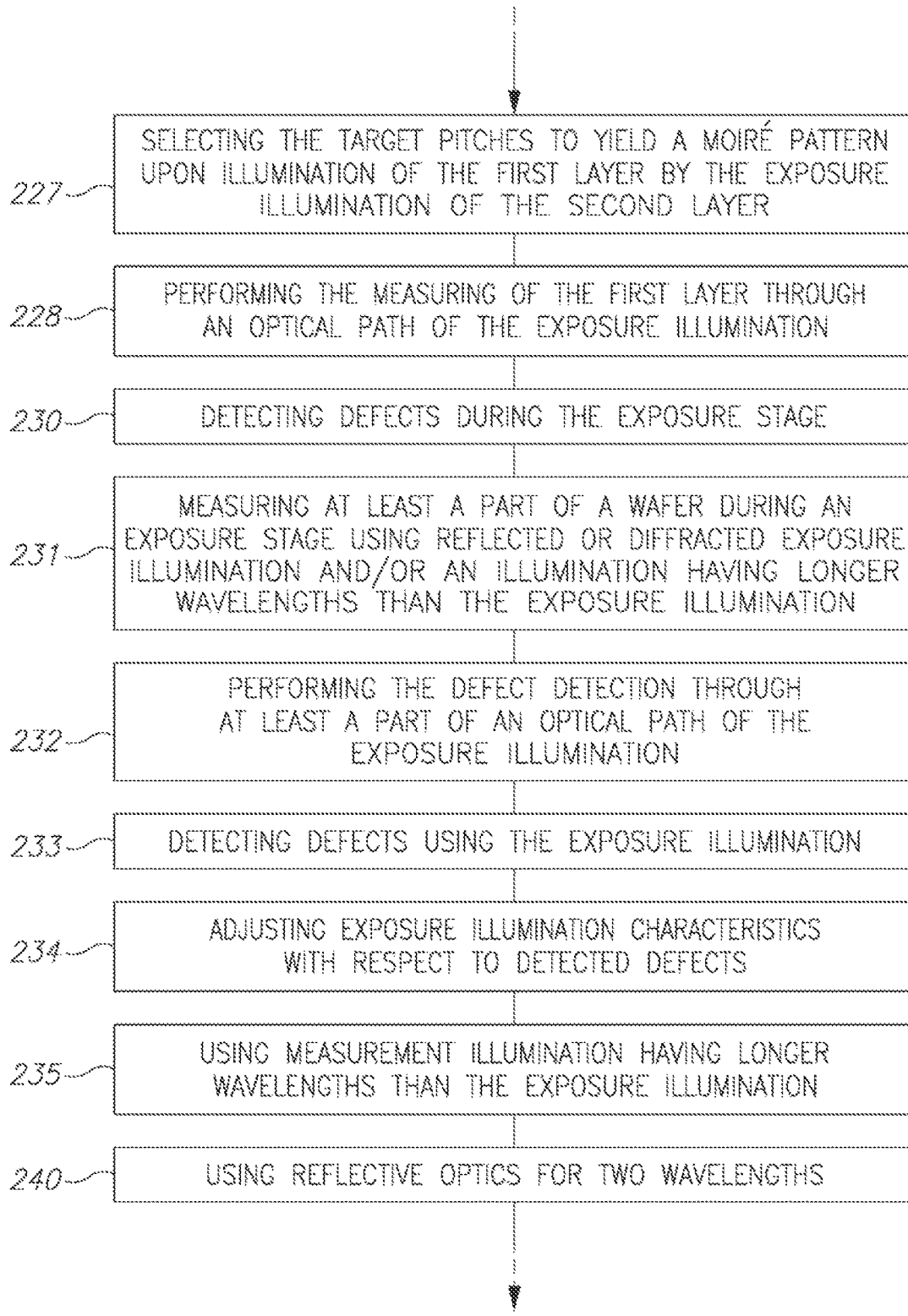
Figure 7 (cont. 1)

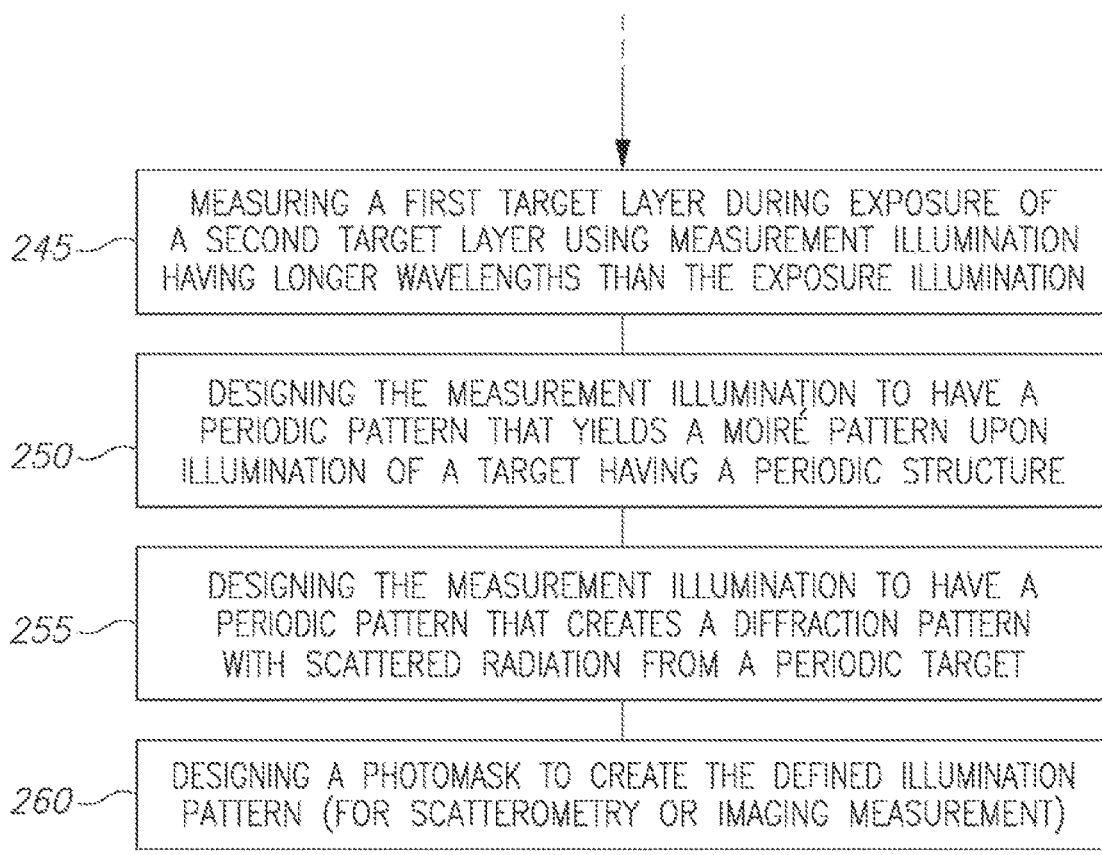
Figure 7 (cont. 2)

IN-SITU METROLOGY

CROSS-REFERENCE TO RELATED APPLICATIONS

This application is a Continuation of International Patent Application Ser. No. PCT/US2013/71143, filed Nov. 21, 2013, which application claims priority of U.S. Provisional Patent Application No. 61/729,327, filed Nov. 21, 2012, which applications are incorporated herein by reference.

FIELD OF THE INVENTION

The present invention relates to the field of metrology, and more particularly, to metrology measurements and process feedback.

BACKGROUND OF THE INVENTION

Current metrology methods are used to measure metrology targets after their production in order to monitor the production and identify production errors. Often this data is fed back to the production tools to correct or adjust production parameters and performance.

SUMMARY OF THE INVENTION

The present invention comprises a metrology method comprising measuring a metrology target during an exposure stage thereof using reflected or diffracted at least one of exposure illumination and an illumination having longer wavelengths than the exposure illumination.

In an embodiment, the present invention comprises a metrology tool arranged to measure a metrology target during an exposure stage thereof using reflected or diffracted at least one of exposure illumination and an illumination having longer wavelengths than the exposure illumination.

A metrology target comprising periodic structures at least a first and a second layer and having correspondingly a first and a second pitch, the first layer being produced prior to the second layer, wherein the first and the second pitches are selected to yield a Moiré pattern upon illumination of the first layer by exposure illumination used in a production of the second layer.

A metrology target having periodic structures at least a first and a second layer and having correspondingly a first and a second pitch, the first layer being produced prior to the second layer, wherein the first and the second pitches are selected to yield a diffraction pattern upon illumination of the first layer by exposure illumination used in a production of the second layer.

A photomask comprising a plurality of pattern elements designed to produce a specified metrology measurements illumination pattern for measuring a metrology target during an exposure stage thereof through the photomask.

A lithography system with a photomask, the photomask having a plurality of pattern elements designed to produce a specified metrology measurements illumination pattern for measuring a metrology target during an exposure stage thereof through the photomask.

A defect detection method comprising measuring at least a part of a wafer during an exposure stage thereof using reflected or diffracted at least one of exposure illumination and an illumination having longer wavelengths than the exposure illumination, to detect defects during the exposure stage.

A defect detection tool arranged to measure at least a part of a wafer during an exposure stage thereof using reflected or diffracted at least one of exposure illumination and an illumination having longer wavelengths than the exposure illumination, to detect defects during the exposure stage.

A lithography system comprising a defect detection tool arranged to measure at least a part of a wafer during an exposure stage thereof using reflected or diffracted at least one of exposure illumination and an illumination having longer wavelengths than the exposure illumination, to detect defects during the exposure stage.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

The nature and mode of operation of the present invention will now be more fully described in the following detailed description of the invention taken with the accompanying drawing Figures, in which:

FIG. 2A is a high level schematic illustration of optical configurations of the lithography system, according to an embodiment of the invention;

FIG. 2B is a high level schematic illustration of optical configurations of the lithography system, according to an embodiment of the invention;

FIG. 3A is a high level schematic illustration of metrology measurements during production using additional illumination, according to an embodiment of the invention;

FIG. 3B is a high level schematic illustration of metrology measurements during production using additional illumination, according to n embodiments of the invention;

FIG. 4A is a high level schematic illustration of metrology measurements during production using the exposure illumination, according to an embodiment of the invention;

FIG. 4B is a high level schematic illustration of metrology measurements during production using the exposure illumination, according to an embodiment of the invention;

FIG. 5A is a high level schematic illustration of metrology measurements of periodic targets during production, according to an embodiment of the invention;

FIG. 5B is a high level schematic illustration of metrology measurements of periodic targets during production, according to an embodiment of the invention;

DETAILED DESCRIPTION OF THE INVENTION

Figure 1A:
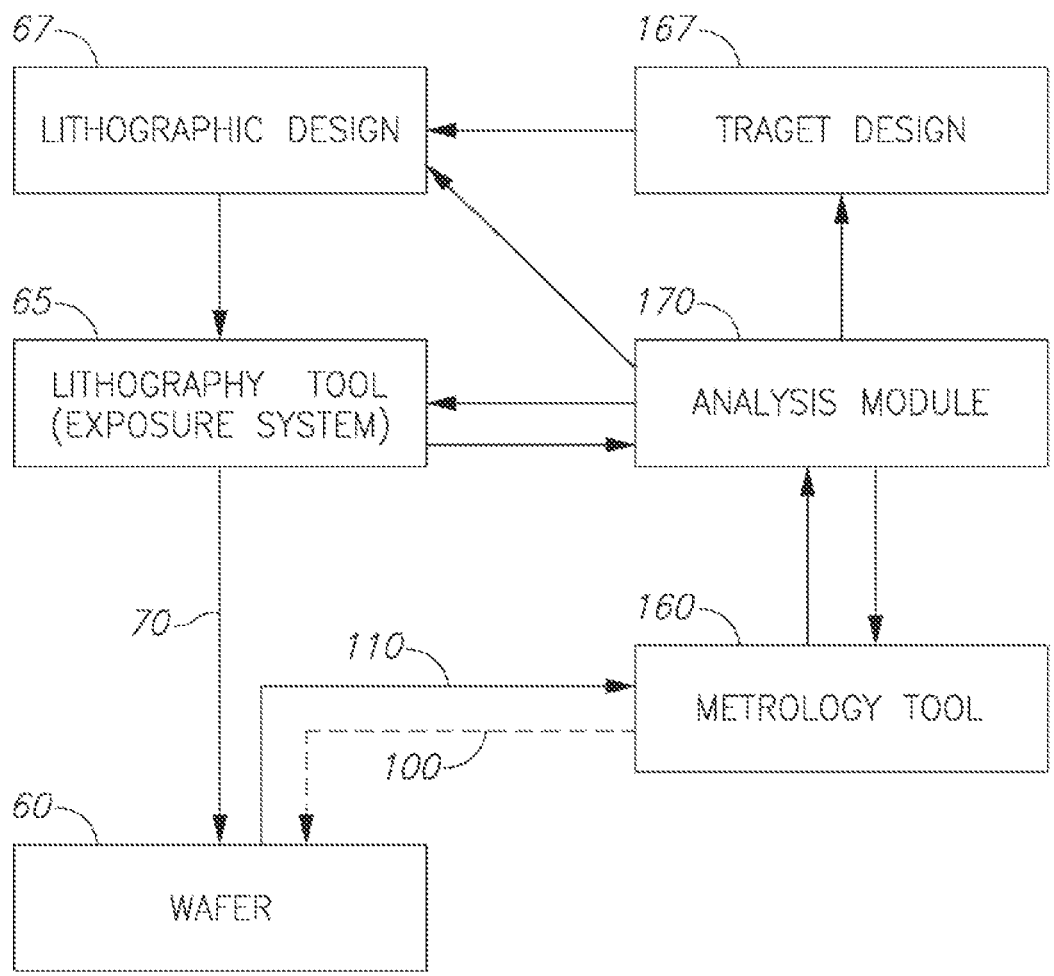
FIG. 1A is a high level schematic block diagram of lithography systems comprising metrology tools, according to an embodiment of the invention.

At the outset, it should be appreciated that like drawing numbers on different drawing views identify identical, or functionally similar, structural elements of the invention. It also should be appreciated that Figure proportions and angles are not always to scale in order to clearly portray the attributes of the present invention.

While the present invention is described with respect to what is presently considered to be the preferred aspects, it is to be understood that the invention as claimed is not limited to the disclosed aspects. The present invention is intended to cover various modifications and equivalent arrangements included within the spirit and scope of the appended claims. In this regard, no attempt is made to show structural details of the invention in more detail than is necessary for a fundamental understanding of the invention. The description taken with the drawings make apparent to those skilled in the art how the several forms of the invention may be embodied in practice.

Furthermore, it is understood that this invention is not limited to the particular methodology, materials and modifications described and, as such, may vary. It is also understood that the terminology used herein is for the purpose of describing particular aspects only, and is not intended to limit the scope of the present invention, which is limited only by the appended claims.

Although any methods, devices or materials similar or equivalent to those described herein can be used in the practice or testing of the invention, the preferred methods, devices, and materials are now described. Meanings of technical and scientific terms used herein are to be commonly understood as by one of ordinary skill in the art to which the invention belongs, unless otherwise defined.

The terms "metrology target" or "target" as used herein in this application, are defined as any structure designed or produced or a wafer which is used for metrological purposes. Non-limiting examples for metrology targets are imaging targets such as a box in a box target and scatterometry targets such as periodic structures (e.g., gratings). The terms "metrology target" or "target" as used herein in this application may refer to any other target design (e.g. AIM (advance image metrology) and variants thereof and alternatives therefor, AIMID, Blossom targets and variants thereof and alternatives therefor, and the like). The terms "metrology target" or "target" as used herein in this application may refer to one or two dimensional targets, or to one or two dimensional target elements.

The terms "metrology measurement" or "measurement" as used herein in this application, are defined as any metrology measurement procedure used to extract information from metrology targets. For example, metrology measurements may be imaging of the targets or scatterometry measurements of the targets. Non-limiting examples for metrology measurements include overlay measurement (imaging or scatterometry), critical dimension (CD) measurement, focus and dose measurement and the like.

The term "scatterometry overlay (SCOL)" as used in this application refers to a metrology method that derives metrology information from the phases of diffraction orders (e.g. the +1 and −1 diffraction orders) that reflect off targets which contain periodic structures such as gratings.

The term "target element" as used herein in this application, is defined as a feature in the metrology target such as individual target areas or boxes, grating bars and the like.

The term "periodic structure" as used in this application refers to any kind of designed or produced structure in at least one layer which exhibits some periodicity. The periodicity is characterized by its pitch, namely its spatial frequency.

The terms "previous layer" and "current layer" as used in this application refer to two layers of a metrology target which are produced sequentially, the current layer upon the previous layer.

The term "exposure illumination" as used in this application refers to the radiation used in the lithographic process to change physical or chemical properties of the wafer at any of its stages.

The terms "lithography tool", "exposure system" and "stepper" as used in this application refer to any tool that applies exposure illumination onto the wafer, such as patterning tools, including scanners, steppers, direct write, and the like. In particular, these terms refer to tools which are distinct from tools which do not expose the wafer to radiation but carry out chemical and physical processing of the wafer, such as a wafer track.

The terms "in-situ measurement" and "in-situ metrology" as used in this application refer to metrology measurements carried out during wafer exposure by a lithography tool. In non-limiting examples, in-situ metrology measurements may refer to metrology measurements carried out using the exposure illumination or reflections thereof, using additional illumination independently from the exposure illumination, or using additional illumination directed through at least a part of the optical path through which the exposure illumination is directed. The measured radiation may also be collected after traversing at least a part of the optical path of the exposure illumination.

Certain embodiments of the invention perform metrology measurements directly on the lithography tool while printing images on the wafer. Such metrology methods are termed in-situ metrology, to enhance their concurrent application with the operation of the lithographic process. In certain embodiments, measurements may be carried out simultaneously with exposure or with respect to the latent image, immediately post exposure on or adjacent to the exposure area on same wafer. Certain embodiments utilize such measurements to establish a very short feedback loop into the lithography stepper (or into any other lithography tool) to correct printing immediately after the measurement (on the same die) or even to apply corrections prior to printing to the exposure parameters (e.g., improve the alignment of current layer to the previous layer). Certain embodiments enable direct layer to layer overlay measurements during the exposure stage of the lithographic process.

FIGS. 1A and 2B are high level schematic flock diagrams of a lithography system 150 comprising a metrology tool 160, according to some embodiments of the invention. in FIG. 1A, which is a highly schematic illustration, a lithography tool 65 uses exposure illumination 70 to carry out a lithographic process on wafer 60, according to a lithographic design 67. Metrology tool 160 may be integrated in the lithographic process by illuminating the produced target with a measurement illumination 100 and measuring reflected or diffracted illumination 110, by measuring reflected or diffracted exposure illumination 110, or by measuring a combination thereof. Illumination by measurement illumination 100 may be carried out simultaneously with illumination by exposure illumination 70.

Metrology tool 160, lithography tool 65 or lithography system 150 may comprise an analysis module 170 arranged to correct the lithographic process during exposure via input to lithography tool 65 and/or prior to the exposure via input to the lithographic design and control 67. Clearly, analysis module 170 may be arranged to correct or enhance metrology target design 167 and its integration into the lithographic design. In certain embodiments, analysis module may be arranged to update target design (e.g., change target design parameters) during production, according to the measuring. In certain embodiments, analysis module 170 may be arranged to correct or change illumination characteristics such as position, intensity, pattern, aperture, and the like. with respect to the measured exposure illumination 70 or measurement illumination 100. Thus, exposure illumination 70 may be corrected during the exposure stage itself to enhance the accuracy of the exposure.

Metrology tool 160 is arranged to measure a metrology target 80 during an exposure stage thereof using either or both reflected or refracted exposure illumination (70→110) and illumination 100 having longer wavelengths than exposure illumination 70 (100→110).

The metrology measurements may be carried out during the pattern formation or a few seconds after the pattern formation. The metrology measurements may comprise measuring any of the following parameters as non-limiting examples: overlay (OVL), critical dimension (CD), focus, doze, defects, aberrations, thickness of resist, and parameters of other layers. In certain embodiments, metrology measurements may comprise detecting defects using the exposure illumination. In particular, the proposed metrology methods, tools and systems may be configured to detect production or exposure defects during exposure, as part of the exposure tool (e.g. stepper 65). In certain embodiments, the metrology measurements may be carried out in a predictive manner i.e. be carried out just before pattern formation or with respect to a previous layer which interacts in the design with current layer Metrology tool 160 may comprise a detect detection tool arranged to measure at least a part of a wafer during an exposure stage thereof using reflected or diffracted at least one of exposure illumination 70 and an illumination having longer wavelengths than the exposure illumination 70, to detect defects during the exposure stage. The defect detection tool may be further arranged to perform the defect detection through at least a part of an optical path of the exposure illumination 70.

Control loops implemented by analysis module 170 may comprise using metrology measurements to correct next printing on the same wafer 60 or on the next wafers 60, and/or to correct before printing on the same field. Control loops implemented by analysis module 170 may involve GDS (Graphic Data System) information, to allow using the known information about previous and current layers for corrections and also for feeding the known information to the next layers.

Figure 1B:
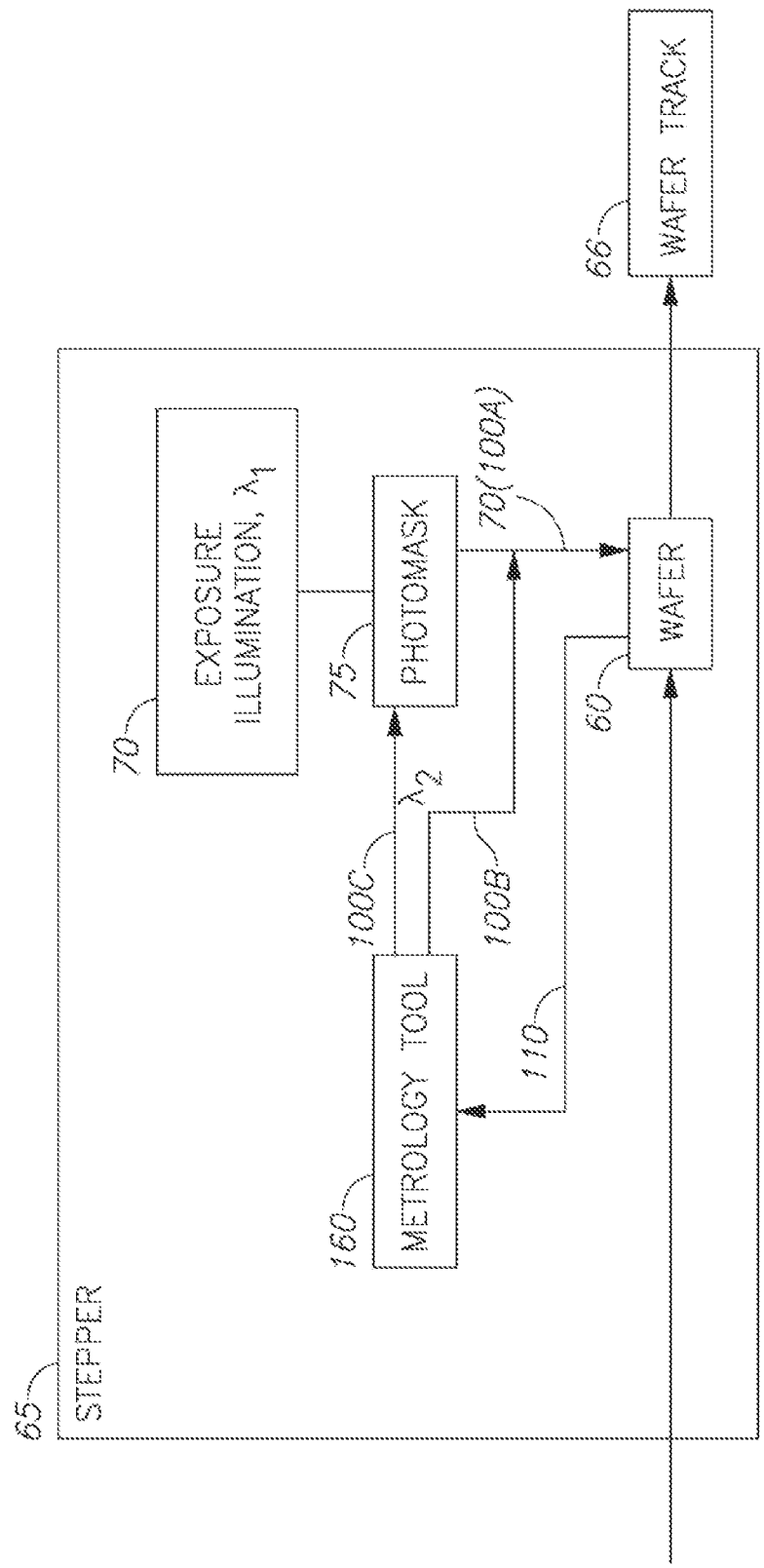
FIG. 1B is a high level schematic block diagram of lithography systems comprising metrology toots, according to an embodiment of the invention.

FIG. 1B is a high level illustration of embodiments in which metrology tool 160 is integrated within lithographic tool 65 such as stepper 65. Stepper 65 receives wafer 60, projects exposure illumination 70 (have a wavelength band denoted by $\lambda_1$) on wafer 60 through photomask 75 and delivers the exposed wafer (e.g., with a latent image in a resist layer) to a wafer track 66 for development. Metrology tool 160 is integrated in stepper 65 and uses either exposure illumination 70 itself as measurement illumination 100A or an additional illumination 100B or 100C, possibly in a different wavelength band (denoted by $\lambda_2$). For example, $\lambda_2$ may be selected according to metrology requirements and in a range that does not influence the wafer and the resist. Measurement illumination 100, when having a different wavelength band may be carried out via a part of the optical axis designed for exposure illumination 70. Measurement illumination 100 may be guided into the optical path after photomask 75 (100B) or before photomask 75 (100C). In the latter case, illumination 100C as well as photomask 75 may be designed to enhance metrology measurements, e.g., by patterning illumination 100C through photomask 75 into illumination pattern 105, as described below. In certain embodiments, measurement illumination 10013 may also be patterned (105).

Advantageously, embodiments of the invention shorten the duration of the feedback loop between the metrology measurements and the lithographic production significantly. In contrast to current methods which apply the results of the metrology measurements to the next wafer to be produced, embodiments of the present invention may be used to apply the metrology results to the next radiation pulse of lithography tool 65 and to correct errors immediately after or even during production. Certain embodiments comprise using predictive methods to apply the metrology correction (prior to exposure, e.g., apply the metrology measurements during patterning and using them to correct the pattern in the same field (die). Certain embodiments comprise metrology targets which are designed to enhance the efficiency of these metrology measurements.

FIGS. 2A and 2B are high level schematic illustrations of optical configurations of lithography system 150, according to some embodiments of the invention. Both Figures illustrate an exposure illumination source 71 directed through an illumination arm 72 and a beam splitter 61 to an objective 51 and to a target 80 on wafer 60. FIG. 2A schematically illustrates directing reflected or diffracted exposure illumination (70→110) through a collection arm 112 to a detector 111 to provide the metrology measurements. FIG. 2B schematically illustrates using an additional illumination source 101 to illuminate (100) target 80 via metrology illumination arm 102, beam splitter 62, beam splitter 61 and objective 51, and directing reflected or diffracted metrology illumination (100→110) through collection arm 112 to detector 111 to provide the metrology measurements. In certain embodiments, metrology tool 160 may be arranged to carry out metrology measurements through an optical path of exposure illumination 70. In certain embodiments, imaging sensor 111 may be positioned in a conjugate optical plane with respect to wafer 60. The optical design illustrated in FIGS. 2A, 2B is a non-limiting illustrative example, which may be realized in various designs that implement the principles described herein In certain embodiments, lithography system 150 may comprise a defect detection tool arranged to measure at least a part of the wafer 60 during an exposure stage thereof using reflected or diffracted at least one of exposure illumination 70 and an illumination having longer wavelengths than the exposure illumination 70, to detect defects during the exposure stage. The defect detection tool may be further arranged to perform the defect detection through at least a part of an optical path of the exposure illumination 70. Lithography system 150 may be arranged to carry out the measuring and the exposure through a common optical path, with the measuring carried out either by reflected or diffracted exposure illumination 110 or by illumination having longer wavelengths than the exposure illumination 70.

FIGS. 3A and 3B are high level schematic illustrations of metrology measurements during production using additional illumination, according to some embodiments of the invention. FIG. 3A is a schematic top view of target 80, FIG. 3B is a schematic cross sectional side view of target 80

In certain embodiments, metrology target 80 comprises at least a first (previous) and a second (current) layer (e.g., layers 90A and 90B with target elements 80A and 80B, respectively). In the illustrated example, first layer 90A is produced prior to second layer 90B. Metrology tool 160 may be arranged to measure first (previous) layer 90A during exposure of second (current) layer 90B using illumination 100. In certain embodiments, illumination 100 may be selected to have longer wavelengths than exposure illumination 70 and thus not interfere in the production process. In non-limiting examples, exposure illumination 70 may be with $\lambda_1$=248 nm, 193 nm, 17 nm, 15 nm or any other wavelength used in exposure systems 65. In non-limiting examples, additional metrology illumination 100 ($\lambda_2$) may be within 200-1500 nm and may be selected with respect to exposure illumination 70 and according to the target design and the metrology requirements.

In certain embodiments, lithography system 150 may be configured to carry out the metrology measurements by illumination 100 having longer wavelengths than exposure illumination 70, and further arranged to direct illumination 100 having longer wavelengths and exposure illumination 70 to target 80 along a common optical path. In certain embodiments, metrology tool 160 may be arranged to carry out metrology measurements through at least a part of the optical path of exposure illumination 70 (the metrology image may be captured via the optical path of exposure tool 65). Previous layer 90A may be imaged using non-exposing radiation 100 while the image of current layer 90B is produced by scattering or reflection of lithographic exposure radiation 70. Enabling optical configurations are, for example, fully reflective optics to eliminate chromatic aberrations, or an optical design restricted to two narrow bands, one ($\lambda_1$) for the stepper illumination band (70) and one ($\lambda_2$) for the additional non-exposing radiation band (100). Alternately, chromatic aberrations between the two images (metrology and lithography) may be corrected by known computational or opto-mechanical methods, In certain embodiments, the optics of lithography tool 65 and metrology tool 160 are partially or fully reflective to diminish or avoid chromatic aberrations (i.e. optical path differences between illumination in $\lambda_1$ and $\lambda_2$). Alternatively or additionally, chromatic aberrations may be compensated for, algorithmically, opto-mechanically or by a combination thereof.

In certain embodiments, any one of target elements 80A, 80B or parts thereof may be measured during the exposure stage. In particular, currently produced target elements 80A, 80B may be simultaneously measured to detect defects, deviations from design and other metrology parameters (overlay, CD, and the like). Reflected or diffracted exposure illumination 110 may be measured to extract metrology parameters concerning the target element 80A, 80B during its exposure.

FIGS. 4A and 4B are high level schematic illustrations of metrology measurements during production using the exposure illumination 70, according to some embodiments of the invention. FIG. 4A is a schematic top view of target 80, FIG. 4B is a schematic cross sectional side view of target 80. Metrology tool 160 may be further arranged to measure first layer 90A during exposure of second layer 90B using exposure illumination 70. In certain embodiments, first (previous) layer 90A may be imaged by exposure illumination 70, e.g., in a specified illumination pattern 105. Specified illumination pattern 105 may be used to distinguish reflected or refracted illumination 110 which related to the metrology measurements. In certain embodiments, specified illumination pattern 105 may be used to create optical patterns upon interaction with target elements 80A, 80B, e.g., as explained below.

In certain embodiments, any one of target elements 80A, 80B or parts thereof may be measured during the exposure stage, in particular, currently produced target elements may be simultaneously measured to detect defects, deviations from design and other metrology parameters (overlay, CD, and the like). Reflected or diffracted exposure illumination 110 may be measured to extract metrology parameters concerning the target element during its exposure.

FIGS. 5A and 5B are high level schematic illustrations of metrology measurements of periodic targets 80 during production, according to some embodiments of the invention. FIG. 5A is a schematic top view of target 80, FIG. 5B is a schematic cross sectional side view of target 80. In certain embodiments, metrology tool 160 may be arranged to measure target 80 (comprising a periodic structure with pitch $P_2$) by illumination 100 having longer wavelengths than exposure illumination 70 or by exposure illumination 70 itself. Illumination 100 or 70 may be designed to have a periodic pattern having a pitch $P_1$ that yields a Moiré pattern upon illumination of the periodic structure in target 80. For example, if pitches $P_1$ (of illumination pattern 105) and $P_2$ (of the target periodic structure) are only slightly different from each other, a Moiré pattern may be created in the pupil plane, having the Moiré pitch $P_{moiré}=P_1 \cdot P_2/(P_1-P_2)$. The creation of such patterns may be used for overlay metrology measurements.

In certain embodiments, metrology target 80 may be designed to comprise periodic structures on at least a first layer 90A and a second layer 90B having correspondingly a first pitch and a second pitch (with first layer 90A produced prior to second layer 90B). The first and the second pitches may be selected to yield a Moiré pattern upon illumination of first layer 90A by exposure illumination 70 used in a production of second layer 90B. In certain embodiments, an existing periodic structure in previous layer 90A may be illuminated by exposing radiation 70 in periodic pattern 105 to produce diffraction of the exposing radiation 70 which is collected either through the exposure tool optics or through dedicated metrology optics. Reflected or refracted illumination 110 may be pupil imaged to provide overlay metrology measurements. In order to separate the signal from different cells, two options are proposed: sequential image cutting in an intermediate image plane on the collection channel, or cells with different periodicity to enable separation in the pupil plane despite simultaneous illumination of the two cells.

Advantageously, direct overlay measurements of layers 90A, 90B is superior in performance to a comparison of overlay measurements of each of these layers to a base layer.

Figure 6A:
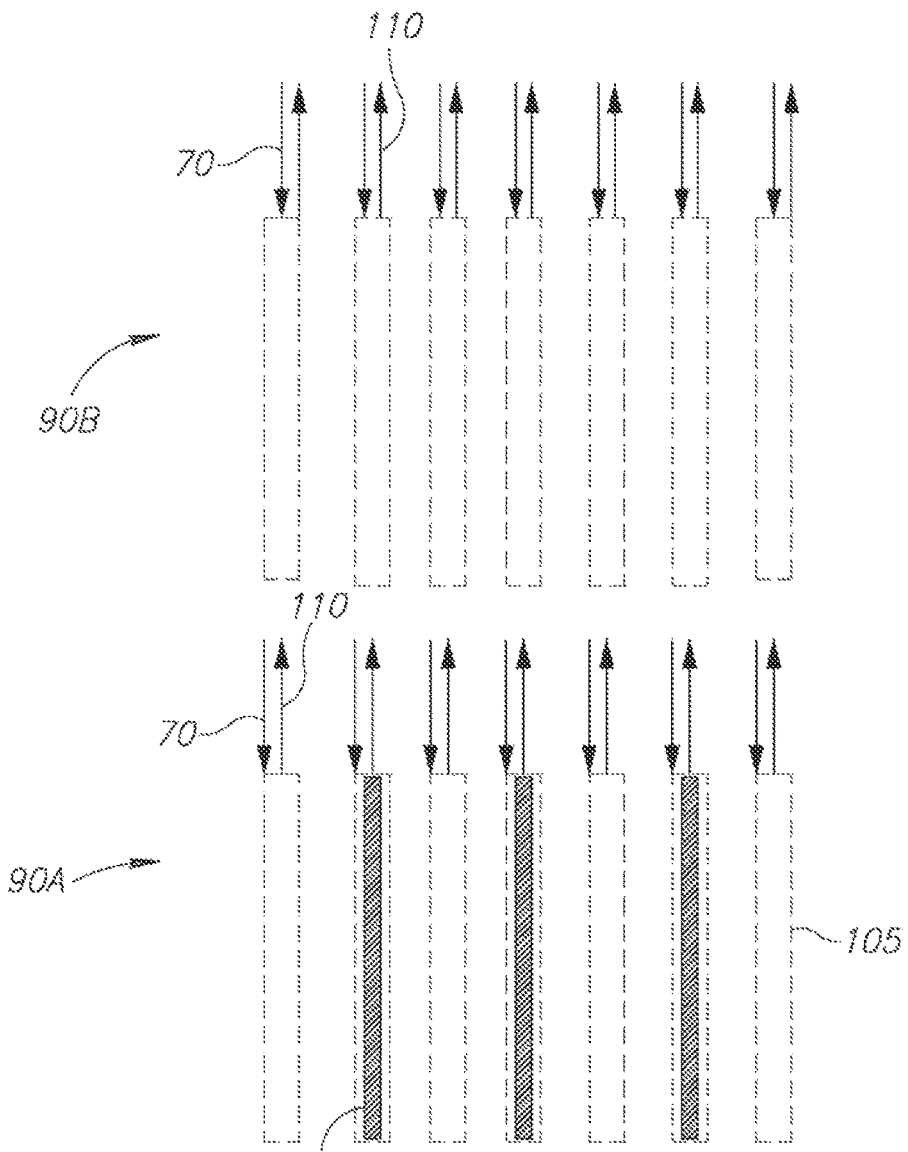
FIG. 6A is a high level schematic illustration of scatterometry measurements of periodic targets during production, according to an embodiment of the invention.
Figure 6B:
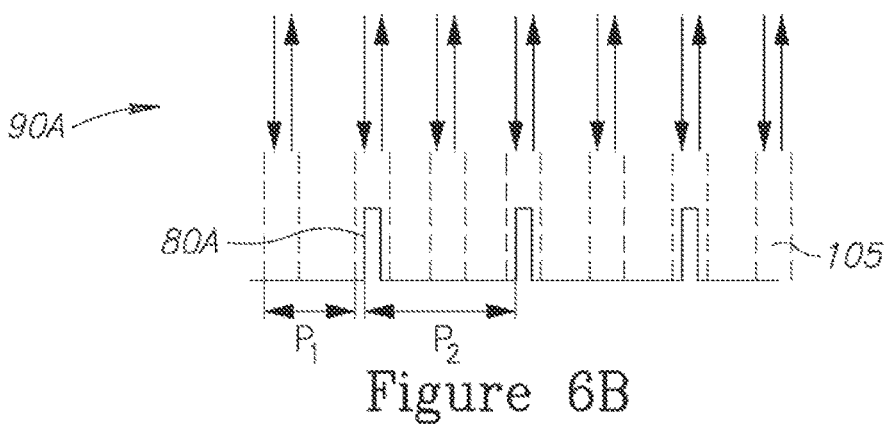
FIG. 6B is a high level schematic illustration of scatterometry measurements of periodic targets during production, according to an embodiments of the invention; and, FIG. 7 is a high level schematic flowchart of a metrology method, according to an embodiment of the invention.

FIGS. 6A and 6B are high level schematic illustrations of scatterometry measurements of periodic targets 80 during production, according to some embodiments of the invention. In the illustrated example, previous layer 90A is measured during the exposure of current layer 90B by exposure illumination 70. Periodic illumination pattern 105 is selected to produce diffraction patterns with reflected or refracted illumination 110. The diffraction patterns are used for the metrology measurements. In certain embodiments, the periodicity of illumination pattern 105 has a simple ratio with the periodicity of target elements 80A in layer 90A (e.g., $P_2/P_1$ is a small integer or a simple fraction of small integers such as ½, ⅓, and the like). The reflected or refracted illumination 110 may be pupil imaged to enable overlay metrology. In order to separate the signal from different cells two options are proposed: sequential image cutting in an intermediate image plane on the collection channel, or cells with different periodicity to enable separation in the pupil plane despite simultaneous illumination of the two cells. Target features 80A, 80B in layers 90A, 90B, respectively, may be similar (same length, same width, same form) or different in any of their parameters.

Figure 7:
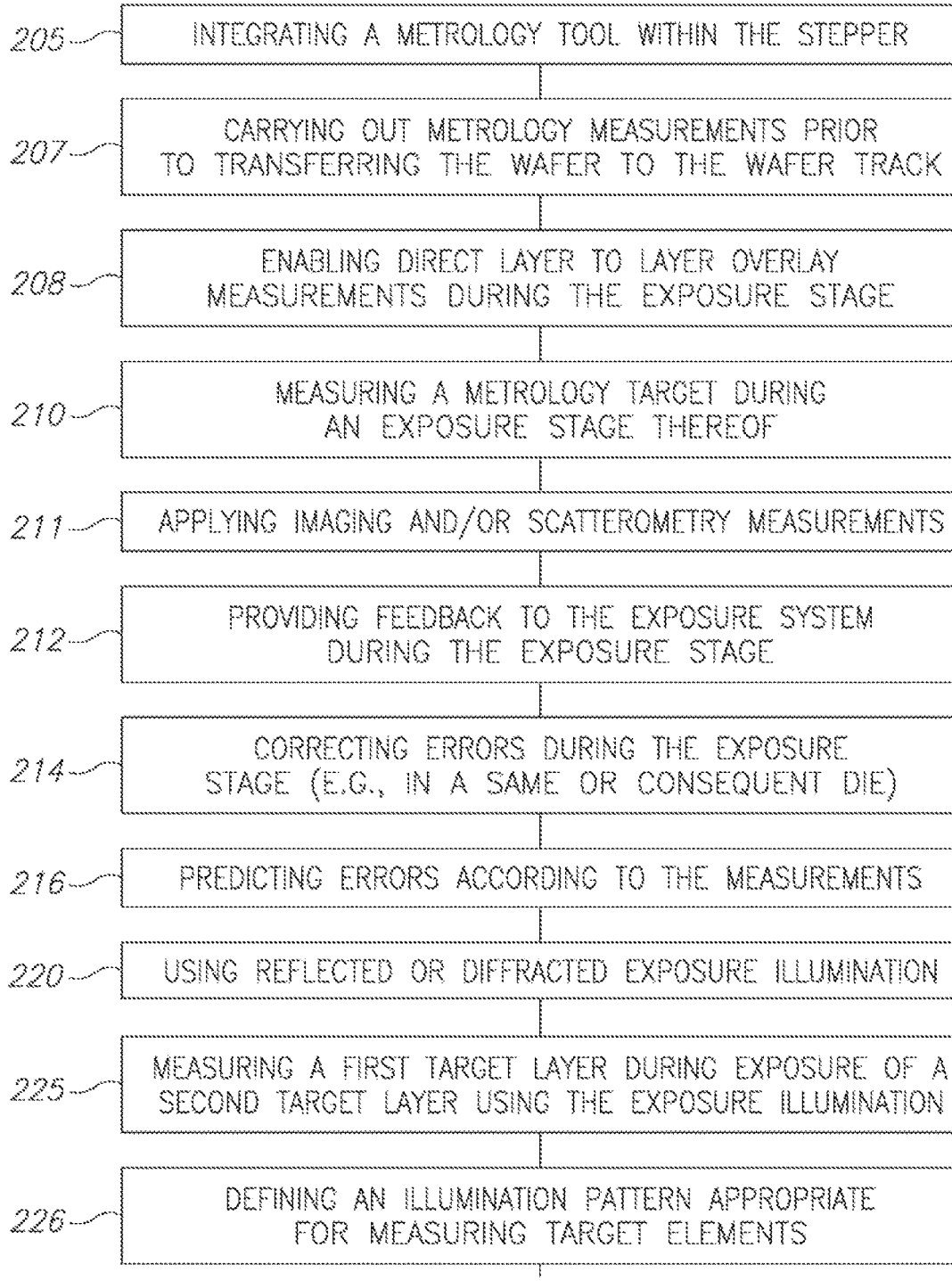

FIG. 7 is a high level schematic flowchart of a metrology method 200, according to some embodiments of the invention. Metrology method 200 may comprise measuring a metrology target during an exposure stage thereof (stage 210) using reflected or diffracted exposure illumination (stage 220) and optionally an illumination having longer wavelengths than the exposure illumination (stage 235). Method 200 may comprise using reflective optics for the two wavelengths (stage 240) in order to diminish or remove chromatic aberrations In certain embodiments, method 200 may comprise integrating a metrology tool within the stepper (stage 205) and carrying out metrology measurements prior to transferring the wafer to the wafer track (stage 207). In certain embodiments, method 200 comprises enabling direct layer to layer overlay measurements during the exposure stage (stage 208).

In certain embodiments, method 200 be applied for imaging and/or scatterometry measurements (stage 211) and may provide feedback to the exposure system during the exposure stage (stage 212), correct errors during the exposure stage (e.g., in a same or consequent die) (stage 214), and even predict errors according to the measurements (stage 216). In certain embodiments, method 200 may comprise correcting, changing, or adjusting illumination characteristics such as position, intensity, pattern, aperture and the like with respect to the measured exposure illumination 70 or measurement illumination 100 according to detected defects (stage 234). Thus, exposure illumination may be corrected during the exposure stage itself to enhance the accuracy of the exposure.

In certain embodiments, the metrology target comprises at least a first and a second layer, the first layer being produced prior to the second layer. Method 200 may further comprise measuring the first layer during exposure of the second layer using the illumination having longer wavelengths than the exposure illumination (stage 245). In certain embodiments, method 200 may further comprise measuring the first layer during exposure of the second layer using the exposure illumination (stage 225).

In certain embodiments, method 200 may comprise a defect detection method comprising detecting defects during the exposure stage (stage 230). Method 200 may comprise measuring at least a part of a wafer during an exposure stage thereof using reflected or diffracted at least one of exposure illumination and an illumination having longer wavelengths than the exposure illumination (stage 231), to detect defects during the exposure stage 230. The defect detection method may further comprise performing the defect detection through at least a part of an optical path of the exposure illumination (stage 232). In certain embodiments, defect detection may be carried out using the exposure illumination (stage 233).

In certain embodiments, method 200 may further comprise performing the measuring of the first layer through at least a part of an optical path of the exposure illumination (stage 228).

In certain embodiments, the metrology target may comprise periodic structures at least a first and a second layer having correspondingly a first and a second pitch, the first layer being produced prior to the second layer. Method 200 may comprise carrying out the measuring by the reflected or diffracted exposure illumination, and further comprise selecting the first and the second pitches to yield a Moiré pattern upon illumination of the first layer by exposure illumination used in the production of the second layer (stage 227). In certain embodiments, in which the measuring is carried out by the illumination having longer wavelengths than the exposure illumination, method 200 may further comprise designing the illumination to have a periodic pattern having a pitch that yields a Moiré pattern upon illumination of the at least one periodic structure (stage 250).

In certain embodiments, method 200 may further comprise defining an illumination pattern appropriate for measuring target elements (stage 226). For example, method 200 may comprise designing the measurement illumination to have a periodic pattern that creates an interference pattern with reflected or diffracted illumination 110 from a periodic target (stage 255). In certain embodiment, method 200 may comprise designing a photomask to create the defined illumination patient (for scatterometry or imaging measurement) (stage 260).

Advantageously, incorporating the metrology measurements into the exposure process is superior to performing metrology measurements at later stages, such as after wafer processing or during non-optical lithography stages (e.g. development stages). Furthermore, certain embodiments provide direct metrology measurements of the produced layers and their spatial relations, which provide accurate and reliable metrology data.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

What is claimed is:
1. A metrology method, comprising:
generating an illumination of a first wavelength, wherein the illumination of a first wavelength is directed along a first optical path;

generating an illumination of a second wavelength, wherein the illumination of a second wavelength is directed along a second optical path, wherein the illumination of a second wavelength is longer than the illumination of a first wavelength;

exposing a metrology target with the illumination of a first wavelength and the illumination of a second wavelength;

measuring the metrology target by collecting at least a portion of illumination emanating from the metrology target in response to at least one of the illumination of the first wavelength or the illumination of the second wavelength, wherein the collected portion of illumination emanates along a third optical path; and correcting at least one characteristic of the illumination of a first wavelength or the illumination of a second wavelength during the exposure of the metrology target based on the metrology target measurement, wherein the first optical path, the second optical path, and the third optical path share at least two optical components.

2. The metrology method of claim 1,
wherein the metrology target comprises a first and a second layer, wherein the first layer is formed prior to the second layer,
wherein the illumination of a second wavelength emanates from the first layer during exposure of the second layer,
wherein the illumination of a second wavelength is measured.

3. The metrology method of claim 1,
wherein the metrology target comprises a first and a second layer, wherein the first layer is formed prior to the second layer,
wherein the illumination of a first wavelength emanates from the first layer during exposure of the second layer,
wherein the illumination of a first wavelength is measured.

4. The metrology method of claim 1,
wherein the illumination of a second wavelength emanates from the metrology target,
wherein the illumination of a second wavelength is measured,
wherein one or more reflective optics are configured to direct the illumination of a second wavelength through at least a portion of the first optical path.

5. The metrology method of claim 1,
wherein the metrology target includes at least two periodic structures, wherein the at least two periodic structures include a first layer with a first pitch and a second layer with a second pitch, wherein the first layer is exposed prior to the second layer,
wherein the first pitch and the second pitch are selected to generate a Moiré pattern upon illumination of the first layer with the illumination of a first wavelength during exposure of the second layer with the illumination of a first wavelength,
wherein the illumination of a first wavelength emanates from the metrology target,
wherein the illumination of a first wavelength is measured.

6. The metrology method of claim 1,
wherein the metrology target includes a periodic structure,
wherein the illumination of a second wavelength reflected, diffracted, or scattered by the metrology target includes a periodic pattern selected to generate a Moiré pattern upon illumination of the periodic structure with the illumination of a second wavelength,
wherein the illumination of a second wavelength is measured.

7. The metrology method of claim 1,
wherein the metrology target includes at least two periodic structures, wherein the at least two periodic structures include a first layer with a first pitch and a second layer with a second pitch, wherein the first layer is exposed prior to the second layer,
wherein the first pitch and the second pitch are selected to generate a diffraction pattern upon illumination of the first layer with the illumination of a first wavelength during exposure of the second layer with the illumination of a first wavelength,
wherein the illumination of a second wavelength emanates from the metrology target,
wherein the illumination of a second wavelength is measured.

8. The metrology method of claim 1, wherein the metrology target includes a periodic structure,
wherein the pitch of the periodic structure is selected to generate a diffraction pattern upon illumination of the periodic structure with the illumination of a second wavelength,
wherein the illumination of a second wavelength emanates from the metrology target,
wherein the illumination of a second wavelength is measured.

9. The metrology method of claim 1, wherein one or more defects are detected during the exposure of the metrology target.

10. The metrology method of claim 9, wherein the one or more defects are detected through at least a part of the first optical path.

11. The metrology method of claim 9, wherein one or more reflective optics are configured to direct the collected portion of illumination reflected, diffracted, or scattered by the metrology target through at least a part of the first optical path.

12. The metrology method of claim 1, wherein the at least two optical components shared by the first optical path, the second optical path, and the third optical path include at least a beam splitter and an objective lens.

13. The metrology method of claim 12, wherein the objective lens is located between the beam splitter and the metrology target in the first optical path, the second optical path, and the third optical path.

14. A system, comprising:
a lithography sub-system, the lithography sub-system configured to:
generate an illumination of a first wavelength to illuminate a metrology target, wherein the illumination of a first wavelength is directed along a first optical path;
generate an illumination of a second wavelength to illuminate the metrology target, wherein the illumination of a second wavelength is directed along a second optical path, wherein the illumination of a second wavelength is longer than the illumination of a first wavelength; and
expose the metrology target with the illumination of a first wavelength and the illumination of a second wavelength;
a metrology sub-system, the metrology sub-system configured to:

measure the metrology target by collecting at least a portion of illumination emanating from the metrology target in response to at least one of the illumination of the first wavelength or the illumination of the second wavelength, wherein the collected portion of illumination emanates along a third optical path, wherein the first optical path, the second optical path, and the third optical path share at least two optical components; and an analysis sub-system, the analysis sub-system configured to:

correct at least one characteristic of the illumination of a first wavelength or the illumination of a second wavelength during the exposure of the metrology target based on the metrology target measurement.

15. The metrology tool of claim 14, wherein the metrology target comprises a first layer and a second layer, wherein the first layer is formed prior to the second layer, wherein the illumination of a second wavelength emanates from the first layer during exposure of the second layer with the illumination of a second wavelength, wherein the illumination of a second wavelength is measured.

16. The metrology tool of claim 14, wherein the metrology target comprises a first layer and a second layer, wherein the first layer is formed prior to the second layer, wherein the illumination of a first wavelength is reflected, diffracted, or scattered from the first layer of the metrology target during exposure of the second layer of the metrology target with the illumination of a first wavelength, wherein the illumination of a first wavelength is measured.

17. The metrology tool of claim 16, wherein the collected potion of illumination reflected, diffracted, or scattered from the first layer of the metrology target is measured through at least a part of the first optical path.

18. The metrology tool of claim 14, wherein the illumination of a second wavelength emanates from the metrology target, wherein the illumination of a second wavelength is measured, wherein one or more reflective optics are configured to direct the illumination of a second wavelength through at least a portion of the first optical path.

19. The metrology tool of claim 14, wherein at least one of the first optical path, the second optical path, or the third optical path includes one or more reflective optics.

20. The metrology tool of claim 14, wherein the metrology target includes a periodic structure, wherein the illumination of a second wavelength reflected, diffracted, or scattered by the metrology target includes a periodic pattern selected to generate a Moiré pattern upon illumination of the periodic structure, wherein the illumination of a second wavelength is measured.

21. The metrology tool of claim 14, wherein one or more defects are detected during the exposure of the metrology target.

22. The metrology tool of claim 21, wherein the one or more defects are detected through at least a part of the first optical path.

23. The system of claim 14, wherein the illumination of a first wavelength emanates from the metrology target, wherein the illumination of a first wavelength is measured.

24. The system of claim 14, wherein the lithography sub-system directs at least a portion of the illumination of a first wavelength and the illumination of a second wavelength along a portion of the second optical path shared with the first optical path.

25. The system of claim 14, further comprising one or more reflective optics.

26. The metrology tool of claim 14, wherein the at least two optical components shared by the first optical path, the second optical path, and the third optical path include at least a beam splitter and an objective lens.

27. The metrology tool of claim 26, wherein the objective lens is located between the beam splitter and the metrology target in the first optical path, the second optical path, and the third optical path.

28. A system, comprising:

a lithography sub-system, the lithography sub-system configured to:

generate an illumination of a first wavelength to illuminate a metrology target, wherein the illumination of a first wavelength is directed along a first optical path;

generate an illumination of a second wavelength to illuminate the metrology target, wherein the illumination of a second wavelength is directed along a second optical path, wherein the illumination of a second wavelength is longer than the illumination of a first wavelength; and expose the metrology target with the illumination of a first wavelength and the illumination of a second wavelength;

a metrology sub-system, the metrology sub-system configured to:

measure the metrology target by collecting at least a portion of illumination emanating from the metrology target in response to at least one of the illumination of the first wavelength or the illumination of the second wavelength, wherein the collected portion of illumination emanates along a third optical path, wherein the first optical path, the second optical path, and the third optical path share at least two optical components; and an analysis sub-system, the analysis sub-system configured to:

correct at least one characteristic of the illumination of a first wavelength or the illumination of a second wavelength during the exposure of the metrology target based on the metrology target measurement; and a wafer track configured to receive exposed wafers from a stepper.

29. The system of claim 28, wherein the at least two optical components shared by the first optical path, the second optical path, and the third optical path include at least a beam splitter and an objective lens.

30. The system of claim 29, wherein the objective lens is located between the beam splitter and the metrology target in the first optical path, the second optical path, and the third optical path.

31. A method for forming and measuring a metrology target, comprising:

forming a first layer, wherein the first layer includes a first plurality of periodic structures having a first pitch; and forming a second layer, wherein the second layer includes a latent image of a second plurality of periodic structures having a second pitch, wherein the first layer is formed prior to the second layer, wherein the first pitch and the second pitch are selected to generate a Moiré pattern upon illumination of the first layer with illumination of a selected wavelength during exposure of the second layer with the illumination of a selected wavelength;

measuring the Moiré pattern; and correcting at least one characteristic of the selected wavelength of illumination while forming the second layer based on the Moiré pattern measurement, wherein the first layer and the second layer are formed by exposing a metrology target with illumination of a first wavelength directed along a first optical path and illumination of a second wavelength directed along a second optical path, wherein the selected wavelength of illumination is either the illumination of a first wavelength or the illumination of the second wavelength, wherein the Moiré pattern is measured by collecting at least a portion of illumination emanating from a metrology target in response to at least one of the illumination of the first wavelength or the illumination of the second wavelength, wherein the collected portion of illumination emanates along a third optical path, wherein the first optical path, the second optical path, and the third optical path share at least two optical components.

32. The method of claim 31, wherein the at least two optical components shared by the first optical path, the second optical path, and the third optical path include at least a beam splitter and an objective lens.

33. The method of claim 32, wherein the objective lens is located between the beam splitter and the metrology target in the first optical path, the second optical path, and the third optical path.

34. A method for forming and measuring a metrology target, comprising:

forming a first layer, wherein the first layer includes a first plurality of periodic structures having a first pitch;

forming a second layer, wherein the second layer includes a latent image of a second plurality of periodic structures having a second pitch, wherein the first layer is formed prior to the second layer, wherein the first pitch and the second pitch are selected to generate a diffraction pattern upon illumination of the first layer with illumination of a selected wavelength during exposure of the second layer with the illumination of a selected wavelength;

measuring the diffraction pattern; and correcting at least one characteristic of the selected wavelength of illumination while forming the second layer based on the diffraction pattern measurement, wherein the first layer and the second layer are formed by exposing a metrology target with illumination of a first wavelength directed along a first optical path and illumination of a second wavelength directed along a second optical path, wherein the selected wavelength of illumination is either the illumination of a first wavelength or the illumination of the second wavelength, wherein the diffraction pattern is measured by collecting at least a portion of illumination emanating from a metrology target in response to at least one of the illumination of the first wavelength or the illumination of the second wavelength, wherein the collected portion of illumination emanates along a third optical path, wherein the first optical path, the second optical path, and the third optical path share at least two optical components.

35. The method of claim 34, wherein the at least two optical components shared by the first optical path, the second optical path, and the third optical path include at least a beam splitter and an objective lens.

36. The method of claim 35, wherein the objective lens is located between the beam splitter and the metrology target in the first optical path, the second optical path, and the third optical path.

37. A method for detecting defects, comprising:

generating an illumination of a first wavelength, wherein the illumination of a first wavelength is directed along a first optical path;

generating an illumination of a second wavelength, wherein the illumination of a second wavelength is directed along a second optical path, wherein the illumination of a second wavelength is longer than the illumination of a first wavelength;

exposing a metrology target with the illumination of a first wavelength and the illumination of a second wavelength;

measuring at least a part of the metrology target by collecting at least a portion of illumination emanating from the metrology target in response to at least one of the illumination of the first wavelength or the illumination of the second wavelength, wherein the collected portion of illumination emanates along a third optical path;

detecting one or more defects generated during the exposure of the metrology target in the metrology target measurement; and correcting at least one characteristic of the illumination of a first wavelength or the illumination of a second wavelength during the exposure of the metrology target based on the detected one or more defects, wherein the first optical path, the second optical path, a the third optical path share at least two optical components.

38. The method of claim 37, wherein the at least two optical components shared by the first optical path, the second optical path, and the third optical path include at least a beam splitter and an objective lens.

39. The method of claim 38, wherein the objective lens is located between the beam splitter and the metrology target in the first optical path, the second optical path, and the third optical path.

40. A system, comprising:

a lithography sub-system, the lithography sub-system configured to:

generate an illumination of a first wavelength to illuminate at least a part of a metrology target, wherein the illumination of a first wavelength is directed along a first optical path;

generate an illumination of a second wavelength to illuminate at least a part of the metrology target, wherein the illumination of a second wavelength is directed along a second optical path, wherein the illumination of a second wavelength is longer than the illumination of a first wavelength; and expose at least a part of the metrology target with the illumination of a first wavelength and the illumination of a second wavelength;

a metrology sub-system, the metrology sub-system configured to:

measure the metrology target by collecting at least a portion of illumination emanating from the metrology target in response to at least one of the illumination of the first wavelength or the illumination of the second wavelength, wherein the collected portion of illumination emanates along a third optical path, wherein the first optical path, the second optical path, and the third optical path share at least two optical components; and an analysis sub-system, the analysis sub-system configured to:

detect one or more defects generated during exposure of the metrology target in the metrology target measurement; and correct at least one characteristic of the illumination of a first wavelength or the illumination of a second wavelength during the exposure of the metrology target based on the detected one or more defects.

41. The system of claim 40, wherein the lithography sub-system directs at least a portion of the illumination of a first wavelength or the illumination of a second wavelength along a portion of the second optical path shared with the first optical path.

42. The system of claim 40, further comprising one or more reflective optics.

43. The system of claim 40, wherein the at least two optical components shared by the first optical path, the second optical path, and the third optical path include at least a beam splitter and an objective lens.

44. The system of claim 43, wherein the objective lens is located between the beam splitter and the metrology target in the first optical path, the second optical path, and the third optical path.

* * * * *